United States Patent [19]

Dau et al.

[11] 4,235,110
[45] Nov. 25, 1980

[54] APPARATUS AND METHOD FOR MEASURING THE CREVICE GAP CLEARANCE IN A HEAT EXCHANGER

[75] Inventors: Gary J. Dau, Palo Alto; Louis J. Martel, Los Altos; Terry D. Scharton, Santa Monica, all of Calif.

[73] Assignee: Electric Power Research Institute, Palo Alto, Calif.

[21] Appl. No.: 2,899

[22] Filed: Jan. 12, 1979

[51] Int. Cl.² ............................................. G01N 19/00
[52] U.S. Cl. ......................................... 73/579; 73/672
[58] Field of Search .................. 73/514, 579, 593, 582, 73/574, 570, 584, 659, 672

[56] References Cited

U.S. PATENT DOCUMENTS

| 3,729,982 | 5/1973 | Senda | 73/579 X |
| 3,860,481 | 1/1975 | Gopal et al. | 73/579 X |

*Primary Examiner*—Jerry W. Myracle
*Attorney, Agent, or Firm*—Flehr, Hohbach, Test, Albritton & Herbert

[57] ABSTRACT

Apparatus and method for measuring the crevice gap clearance between the tubes and tube supports in a heat exchanger includes setting the tube into vibration until it impacts against the tube support plate and determining by accelerometers mounted on the tube the distance the tube has moved.

5 Claims, 16 Drawing Figures

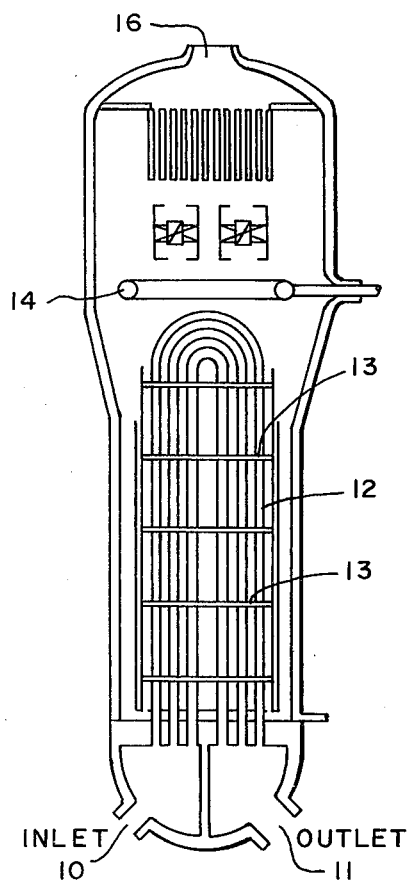
FIG.—1
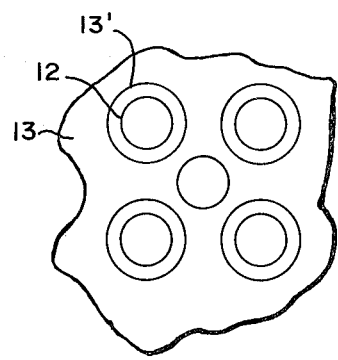
FIG.—2
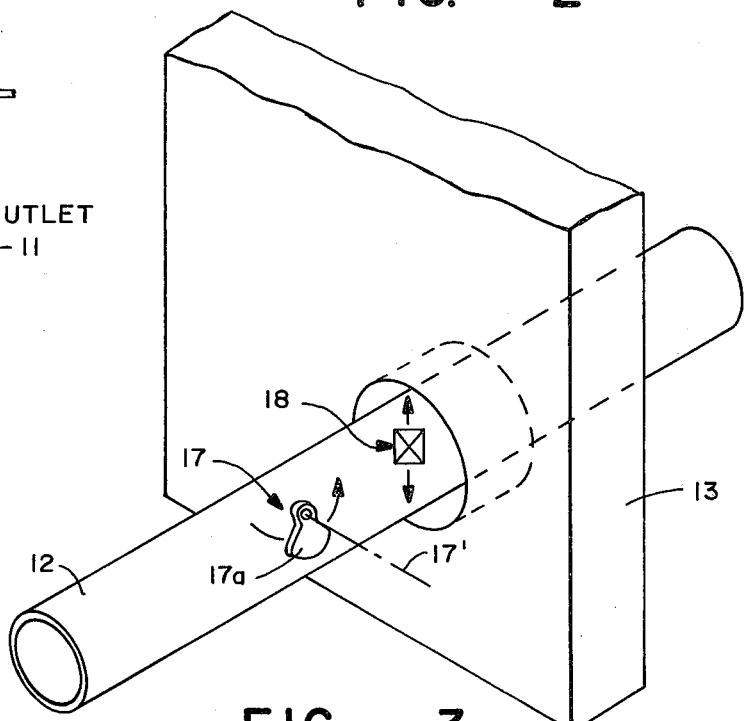
FIG.—3
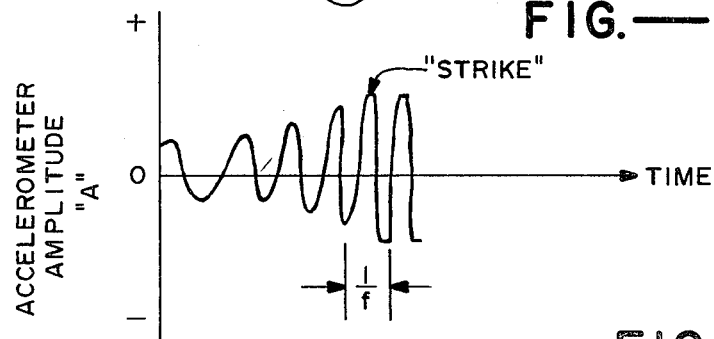
FIG.—4

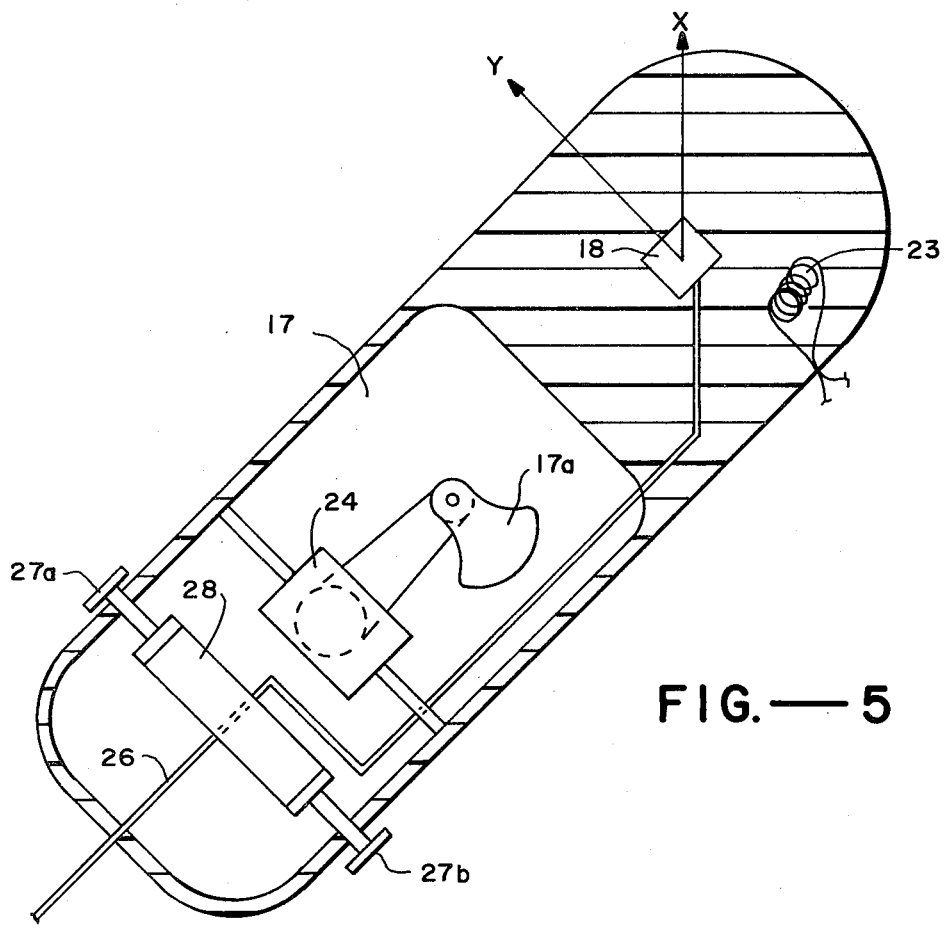
FIG.—5
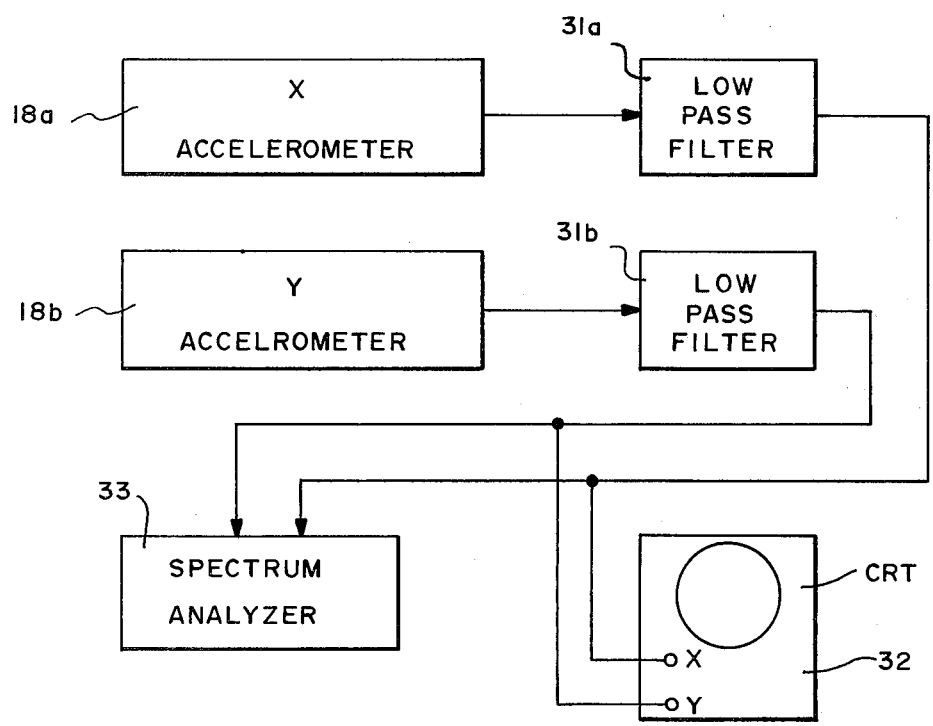
FIG.—6

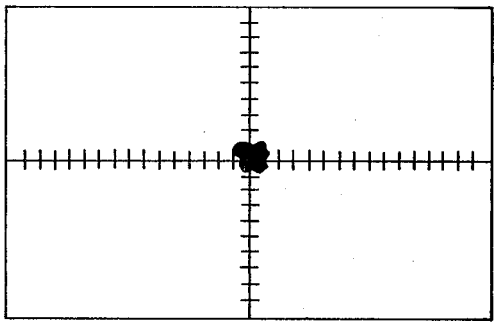
1 MIL CLEARANCE
33 Hz, 7.3 MILS/DIV.
FIG.—7A
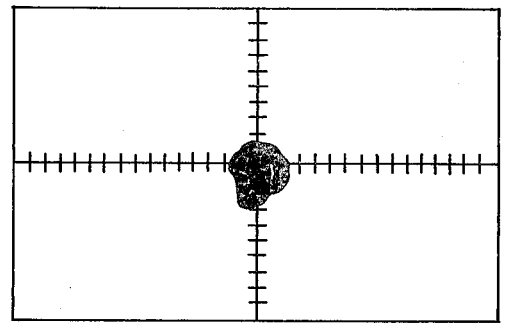
3 MIL CLEARANCE
104 Hz, 2.2 MILS/DIV.
FIG.—7B
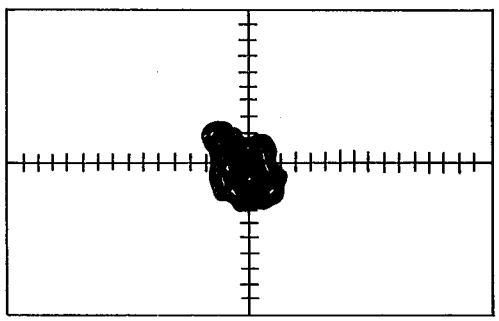
6 MIL CLEARANCE
33 Hz, 7.3 MILS/DIV.
FIG.—7C
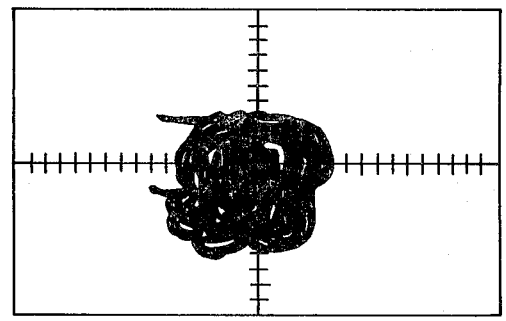
10 MIL CLEARANCE
36 Hz, 6.1 MILS/DIV.
FIG.—7D
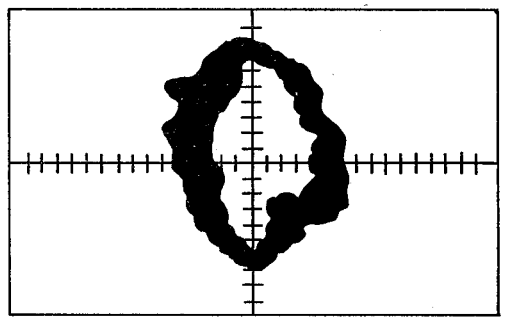
20 MIL CLEARANCE
36 Hz, 6.1 MILS/DIV.
FIG.—7E
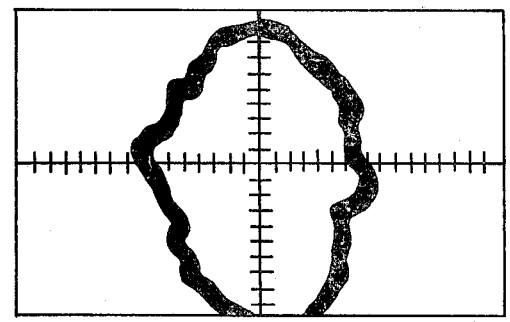
30 MIL CLEARANCE
36 Hz, 6.1 MILS/DIV.
FIG.—7F

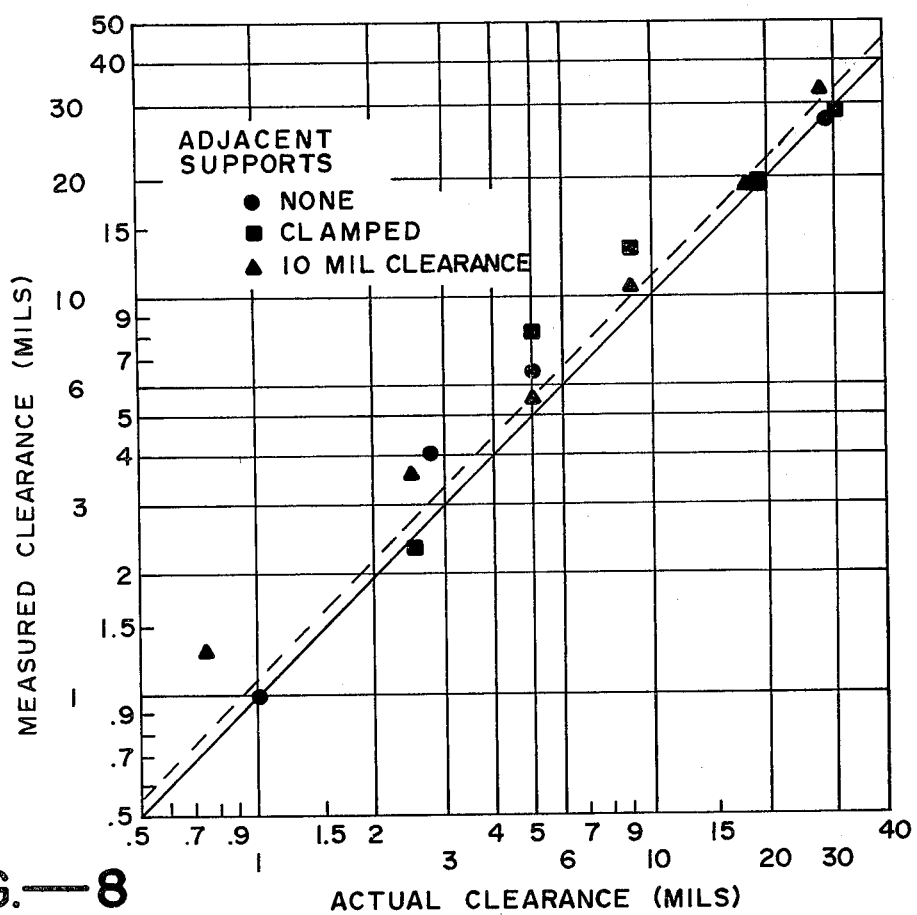
FIG.—8
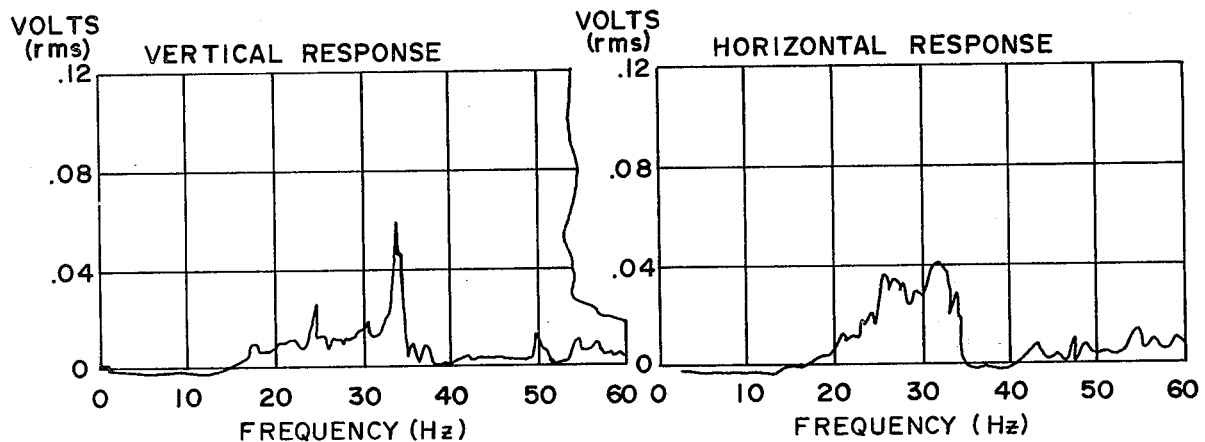
FIG.—9A    FIG.—9B
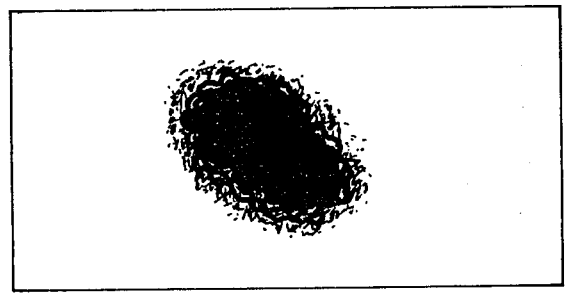
FIG.—10

APPARATUS AND METHOD FOR MEASURING THE CREVICE GAP CLEARANCE IN A HEAT EXCHANGER

BACKGROUND OF THE INVENTION

The present invention is directed to an apparatus and method for measuring the crevice gap clearance in a heat exchanger and more particularly for steam generators used in nuclear power plants.

Currently many steam generators used in nuclear power plants suffer corrosion problems in the gap between a heat exchange tube and a tube support plate. Buildup of these corrosion products has many bad side effects including denting of the tube, or constricting it to a smaller diameter which causes cracks and developing leaks. Thus in order to obtain an early warning of the onset of denting, etc. it is desirable to measure the clearance between the tube outer diameter and the tube support plate. Ultrasonic and eddy current techniques have been attempted but have not proved satisfactory.

Moreover, it may also be possible to chemically clean or reverse the buildup of corrosion. Thus a technique for indicating when chemical cleaning should be applied and thereafter measuring the effect of such chemical cleaning is also highly desirable.

OBJECTS AND SUMMARY OF THE INVENTION

It is, therefore, a general object of the present invention to provide a method for measuring the crevice gap clearance in a heat exchanger.

It is a more specific object to provide a method and also apparatus which is specifically applicable to the steam generators of nuclear type power plants.

It is yet another object of the invention to provide a method which is nondestructive in nature.

In accordance with the above objects there is provided a method of measuring the crevice gap clearance between a tube and tube support in heat exchangers. The tube is vibrated in proximity to the tube support and the acceleration monitored in the tube support region. The clearance is determined from such monitored acceleration.

Alternatively from an apparatus standpoint there is provided an apparatus for measuring the crevice gap clearance between a tube and a tube support in heat exchangers. An elongated unitary structure is inserted in the tube which carries means for setting the tube into vibratory motion in proximity to the tube support and means to sense the acceleration of the vibratory motion. Means are also provided for processing the sensed acceleration to determine the clearance.

BRIEF DESCRIPTION OF THE DRAWINGS

FIG. 1 is a cross-sectional view illustrating a steam generator;

FIG. 2 is a greatly enlarged cross-sectional detailed view of FIG. 1 showing tubes passing through a tube support plate;

FIG. 3 is a simplified perspective view illustrating the present invention;

FIG. 4 is a waveform characteristic useful in understanding the present invention;

FIG. 5 is a partially cross-sectional broken away view of apparatus used in practicing the present invention;

FIG. 6 is a block diagram embodying the present invention;

FIGS. 7A through 7F are oscilloscope patterns useful in understanding the present invention;

FIG. 8 is a graph;

FIGS. 9A and 9B are spectrum analysis plots; and

FIG. 10 is a lissajous figure.

DETAILED DESCRIPTION OF THE PREFERRED EMBODIMENTS

FIG. 1 illustrates a typical U-bend steam generator configuration. The primary reactor coolant inlet of heated fluid from the nuclear reactor is at 10 and the outlet is at 11. Three pairs of U-bend tubes 12 are indicated which are supported by horizontal plates 13. Feedwater from a condenser enters the generator at 14, is heated by the coolant circulating through the tubes 12, and exits as steam to the turbine at 16. In summary, FIG. 1 illustrates a typical saturated steam generator used in nuclear power generation.

FIG. 2 illustrates a portion of a support plate 13 having holes 13' through which tubes 12 pass. As discussed above corrosion tends to form at these points. FIG. 3 illustrates in more graphic form FIG. 2 showing the support plate 13 with a tube 12. However, in accordance with the invention there is illustrated as mounted within the tube 12 a vibrator 17 along with accelerometers 18. The accelerometer has an axis of rotation shown as 17' which is perpendicular to the tube axis. However, this could alternatively be parallel to the tube axis. The vibrator 17 includes an eccentric mass 17a which thus forms an eccentric weight shaker which will set tube 12 into vibration when actuated either by an associated electric motor or an air turbine. Accelerometers 18 are mounted in the tube also and would typically be located at a 90° angle to each other.

FIG. 4 illustrates operation of the invention where when the tube is set into vibration the accelerometer signal amplitude "A" increases until a strike occurs with the support plate 13. At this point by determination of the frequency and the use of the accelerometer signal amplitude a crevice gap may be determined by the following equation.

$$\text{Crevice Gap} = A/(2\pi f_s)^2$$

where $f_s$ is the strike frequency.

The actual apparatus for retaining the vibrator 17 and the accelerometers 18 in a unitary structure is illustrated in FIG. 5. Here there is an elongated bulletshaped shell 21 which has a diameter smaller than the tube 12 which is basically constructed at its tip 22 of rigid hard rubber or silicon. Mounted at the tip end are the accelerometers 18. In addition, there is eddy current unit 23 which senses the large metal mass of support plate 13 (see FIG. 3) to determine when the accelerometers 18 and the vibrator 17 are in proximity to the tube support plate. In other words, the entire structure 21 is passed into the tube until in proximity to a tube support plate. Alternatively, of course, simple measurement techniques could be utilized.

Vibrator 17 is illustrated with a motor 24 and, of course, the eccentric mass 17a. Appropriate lead wires indicated at 26 are provided. In addition to retain the unit 21 and the tube at the proper location there are a pair of friction pads 27a,b which are driven against the sides of the tube by a pneumatic cylinder 28.

FIG. 6 illustrates the X and Y accelerometers 18a and 18b and the associated electronics to analyze the output signals of the accelerometers. These include a pair of low pass filters 31a,b which filter out high frequency components caused by the impact of the tube with its tube support. In other words, it is the low frequency components which contain information which is of interest. The outputs of the filters may be applied either to a cathode ray tube 32 and specifically the X and Y inputs to form a lissajous figure or pattern and/or in addition, a spectrum analyzer unit 33. Typical outputs for lissajous figures for a CRT are illustrated in FIGS. 7A through 7F with the clearances and frequencies and relative scale of the CRT given. Note that these figures are produced by several repetitions and thus are produced by storage oscilloscope.

FIG. 8 is a plot of FIGS. 7A through 7F and specifically the squares indicating clamped date points. In other words, when these data points were taken an experimental tube was clamped at its two ends and allowed to vibrate against a central support plate. The horizontal axis of the graph of FIG. 8 illustrates the actual clearance between the tube and the tube support plate and the vertical axis is measured clearance in mils. Obviously the 45° line 34 would be the optimum relationship between actual and measured clearance. On an experimental basis the curves of FIGS. 7A through 7F were plotted along with the diamond-shaped points where a 10 mil clearance was provided at the adjacent supports; the circle is where they were free. The resulting dashed line 36 illustrates the accuracy of the method in that a constant correction could be applied. The data points of FIG. 8 were actually obtained by measuring on the polar coordinate basis FIGS. 7A through 7F and effectively taking the maximum points.

FIGS. 9A and 9B illustrate an alternative to the lissajous pattern technique and are spectrum analysis plots of FIG. 7C. This is accomplished by the spectrum analyzer 33 of FIG. 6 and the appropriate data points for vertical and horizontal responses are indicated to yield data points similar to those of FIG. 8.

Another experimental lissajous pattern is illustrated in FIG. 10 which is the response of a tube impacting on the center support plate with excitation at 120 Hz with 0.4# force. Here the high frequency components caused by the impact of a tube with the tube support are clearly shown and are filtered out by the appropriate filters 31a,b of FIG. 6. It is obvious that the lissajous figures are, of course, necessarily formed by time varying monitored acceleration signals which have a phase difference between them because of their orthogonal displacement.

From an equipment point of view the accelerometers may be of the type sold under the trademark BOLT, BERANEK and NEWMAN Model 501. These accelerometers have a flat frequency response from 2 Hz to 50,000 Hz and the sensitivity of 100 mv per g.

Thus an effective technique for measuring crevice gap has been provided. It is applicable to all types of heat exchangers including condensers and transformer coolers as well as steam generators.

What is claimed is:

1. A method of measuring the crevice gap clearance between a tube and a tube support in heat exchangers and the like comprising the following steps: vibrating such tube in proximity to said tube support; monitoring the acceleration of such tube in the tube support region; and determining from such monitored acceleration said clearance.

2. A method as in claim 1 where said determination is made by the step of processing two time varying monitored acceleration signals having a phase difference and forming a lissajous pattern.

3. A method as in claim 1 where said determination is made by a spectral analysis of said monitored acceleration.

4. Apparatus for measuring the crevice gap clearance between a tube and a tube support in heat exchangers and the like comprising: an elongated unitary structure insertable in such tube and carrying means for setting such tube into vibratory motion in proximity to said tube support and carrying means for sensing the acceleration of such vibratory motion; and means for processing said sensed acceleration to determine said clearance.

5. Apparatus as in claim 4 together with eddy current sensor carried by said unitary structure for sensing the proximity to said tube support.

* * * * *